United States Patent
Lowery et al.

[11] Patent Number: 5,979,472
[45] Date of Patent: Nov. 9, 1999

[54] TOY WASHER AND DISINFECTOR DEVICE

[76] Inventors: Ginger E. Lowery, 630 S. Old Belair Rd., #14, Grovetown, Ga. 30813; Thomas M. Fassuliotis, 4085 Cochran Rd., Gainesville, Ga. 30506

[21] Appl. No.: 09/067,986

[22] Filed: Apr. 29, 1998

[51] Int. Cl.[6] .................................................. B08B 3/10
[52] U.S. Cl. ..................... 134/58 R; 134/95.2; 134/99.2; 134/105; 134/147; 134/153; 134/102.3; 422/297; 422/300
[58] Field of Search ............................. 134/58 R, 58 D, 134/95.2, 99.2, 105, 147, 153, 158, 102.3; 422/281, 284, 291, 297, 300, 24

[56]     References Cited

U.S. PATENT DOCUMENTS

| | | | |
|---|---|---|---|
| 1,893,797 | 1/1933 | Foster | 134/58 |
| 2,592,117 | 4/1952 | Chadwick | 134/141 |
| 3,020,917 | 2/1962 | Lyman | 134/58 |
| 3,021,702 | 2/1962 | Houser | 68/207 |
| 3,203,436 | 8/1965 | Wallgren | 134/58 |
| 3,207,167 | 9/1965 | Edstrom | 134/144 |
| 3,384,098 | 5/1968 | Swetnam | 134/58 |
| 3,460,550 | 8/1969 | Zanussi | 134/112 |
| 3,680,570 | 8/1972 | Nobili | 134/134 |
| 3,760,823 | 9/1973 | Ferguson | 134/141 |
| 4,286,395 | 9/1981 | Hoersch | 34/155 |
| 4,329,596 | 5/1982 | Marcade | 307/141.8 |
| 4,468,600 | 8/1984 | Barthel | 318/452 |
| 5,332,388 | 7/1994 | Schuerch | 422/291 |
| 5,398,707 | 3/1995 | Harris | 134/58 R |
| 5,500,050 | 3/1996 | Chan | 134/18 |
| 5,545,335 | 8/1996 | Sween | 210/748 |
| 5,660,195 | 8/1997 | Taylor | 134/58 D |
| 5,762,080 | 6/1998 | Edwards | 134/58 D |

*Primary Examiner*—Frankie L. Stinson

[57]     ABSTRACT

A toy washing and disinfecting device for washing and disinfecting a variety of toys, particularly at locations such as doctors waiting rooms and child care facilities where large numbers of children can come in contact with the toys. To increase the likelihood of use, the toy washing and disinfector device functions automatically in the manner of a dishwasher.

1 Claim, 3 Drawing Sheets

TOY WASHER AND DISINFECTOR DEVICE

TECHNICAL FIELD

The present invention relates to cleaning and sanitizing devices and more particularly to a toy washer and disinfector device for cleaning and disinfecting toys, such as at a child care center, that includes two disinfecting mechanisms; the toy washer and disinfector device including a housing assembly including a lower housing portion and an upper housing portion; a washing and disinfecting chamber formed within the lower housing portion; a water supply control valve for supplying water to the washing and disinfecting chamber; a sewer line drain control valve for draining water and soap from the washing and disinfecting chamber; a sealable chamber access door pivotally connected to the lower housing portion; a light disinfection mechanism including a plurality of ultraviolet light disinfecting assemblies, each ultraviolet light disinfecting assembly including a tempered glass window set into the interior chamber wall and an ultraviolet emitting light; a plurality of user removable, rotatable item racks rotatably disposed on a spray tower positioned within the washing and disinfecting chamber; a spray tower pump unit including an inlet in connection with the washing and disinfecting chamber and an outlet in connection with the spray tower; a chemical disinfecting mechanism including a bleaching unit having a bleach reservoir, a bleach dispensing pump, and a bleach dispensing nozzle; a washing soap dispensing assembly; a dryer mechanism including a forced heated air blower and exhaust vent; a chamber heating element positioned within the washing and disinfecting chamber; and timer and function controls positioned within the upper housing portion, including a defective ultraviolet light indicator lamp and an on/off switch, and in controlling connection with the light disinfection mechanism, the chemical disinfecting mechanism, the washing soap dispensing assembly, the dryer mechanism, the heating element, the spray tower pump unit, the water supply valve, and the sewer drain line valve; the timer and function controls controlling a light disinfection cycle, a chemical disinfecting cycle, a soap wash cycle, a clean water rinse cycle, and a drying cycle.

BACKGROUND ART

Because disease can be transmitted through contact with physical items such as toys, it would be desirable to have a toy washing and disinfecting device for washing and disinfecting a variety of toys, particularly at locations such as doctors waiting rooms and child care facilities where large numbers of children can come in contact with the toys. To increase the likelihood of use, it would of course be a benefit to have a toy washing and disinfector device that functioned automatically in the manner of a dishwasher.

GENERAL SUMMARY DISCUSSION OF INVENTION

It is thus an object of the invention to provide a toy washer and disinfector device that can clean multiple toys.

It is a further object of the invention to provide a toy washer and disinfector device that operates automatically.

It is a still further object of the invention to provide a toy washer and disinfector device that has removable toy racks that are positionable within a washing and disinfecting chamber.

It is a still further object of the invention to provide a toy washer and disinfector device that includes a housing assembly including a lower housing portion and an upper housing portion; a washing and disinfecting chamber formed within the lower housing portion; a water supply control valve for supplying water to the washing and disinfecting chamber; a sewer line drain control valve for draining water and soap from the washing and disinfecting chamber; a sealable chamber access door pivotally connected to the lower housing portion; a light disinfection mechanism including a plurality of ultraviolet light disinfecting assemblies, each ultraviolet light disinfecting assembly including a tempered glass window set into the interior chamber wall and an ultraviolet emitting light; a plurality of user removable, rotatable item racks rotatably disposed on a spray tower positioned within the washing and disinfecting chamber; a spray tower pump unit including an inlet in connection with the washing and disinfecting chamber and an outlet in connection with the spray tower; a chemical disinfecting mechanism including a bleaching unit having a bleach reservoir, a bleach dispensing pump, and a bleach dispensing nozzle; a washing soap dispensing assembly; a dryer mechanism including a forced heated air blower and exhaust vent; a chamber heating element positioned within the washing and disinfecting chamber; and timer and function controls positioned within the upper housing portion, including a defective ultraviolet light indicator lamp and an on/off switch, and in controlling connection with the light disinfection mechanism, the chemical disinfecting mechanism, the washing soap dispensing assembly, the dryer mechanism, the heating element, the spray tower pump unit, the water supply valve, and the sewer drain line valve; the timer and function controls controlling a light disinfection cycle, a chemical disinfecting cycle, a soap wash and clean water rinse cycle, and a drying cycle.

It is a still further object of the invention to provide a toy washer and disinfector device that accomplishes some or all of the above objects in combination.

Accordingly, a toy washer and disinfector device is provided. The toy washer and disinfector device includes a housing assembly including a lower housing portion and an upper housing portion; a washing and disinfecting chamber formed within the lower housing portion; a water supply control valve for supplying water to the washing and disinfecting chamber; a sewer line drain control valve for draining water and soap from the washing and disinfecting chamber; a sealable chamber access door pivotally connected to the lower housing portion; a light disinfection mechanism including a plurality of ultraviolet light disinfecting assemblies, each ultraviolet light disinfecting assembly including a tempered glass window set into the interior chamber wall and an ultraviolet emitting light; a plurality of user removable, rotatable item racks rotatably disposed on a spray tower positioned within the washing and disinfecting chamber; a spray tower pump unit including an inlet in connection with the washing and disinfecting chamber and an outlet in connection with the spray tower; a chemical disinfecting mechanism including a bleaching unit having a bleach reservoir, a bleach dispensing pump, and a bleach dispensing nozzle; a washing soap dispensing assembly; a dryer mechanism including a forced heated air blower and exhaust vent; a chamber heating element positioned within the washing and disinfecting chamber; and timer and function controls positioned within the upper housing portion, including a defective ultraviolet light indicator lamp and an on/off switch, and in controlling connection with the light disinfection mechanism, the chemical disinfecting mechanism, the washing soap dispensing assembly, the dryer mechanism, the heating element, the spray tower pump unit, the water supply valve, and the sewer drain line valve; the timer and function controls controlling a light disinfection cycle, a chemical disinfecting cycle, a soap wash and clean water rinse cycle, and a drying cycle.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
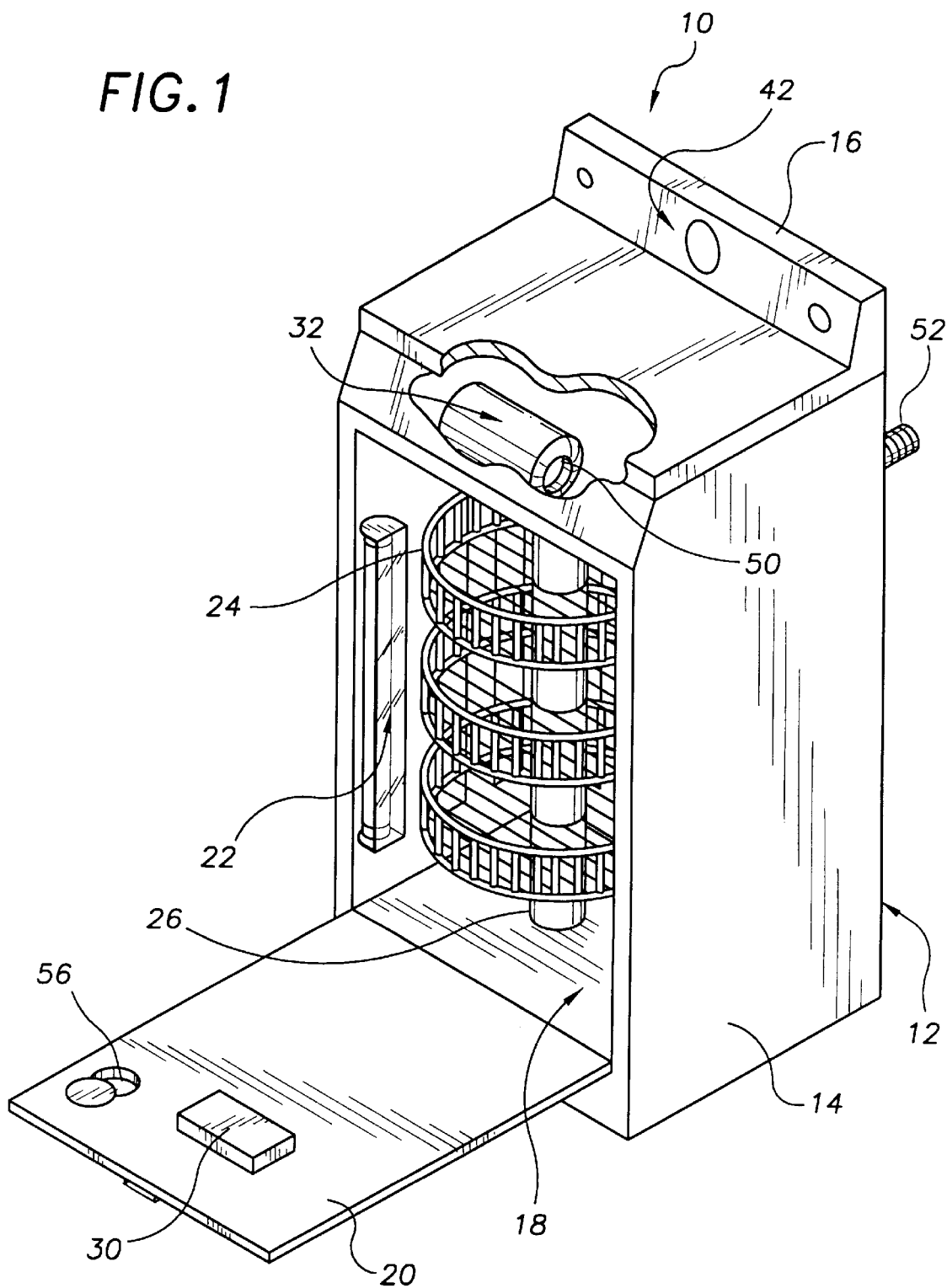
FIG. 1 is a partial cut-away perspective view of an exemplary embodiment of the toy washer and disinfector device of the present invention showing a housing assembly including the lower housing portion and the upper housing portion; the washing and disinfecting chamber formed within the lower housing portion; the sealable chamber access door; several of the ultraviolet light disinfecting assemblies of the light disinfection mechanism, each ultraviolet light disinfecting assembly including a tempered glass window set into the interior chamber wall; three user removable, rotatable item racks rotatably disposed on the spray tower; the bleaching unit dispensing nozzle; the washing soap dispensing assembly; the forced heated air blower and exhaust vent of the dryer mechanism; the timer and function controls positioned within the upper housing portion; the defective ultraviolet light indicator lamp; and the on/off switch.
Figure 2:
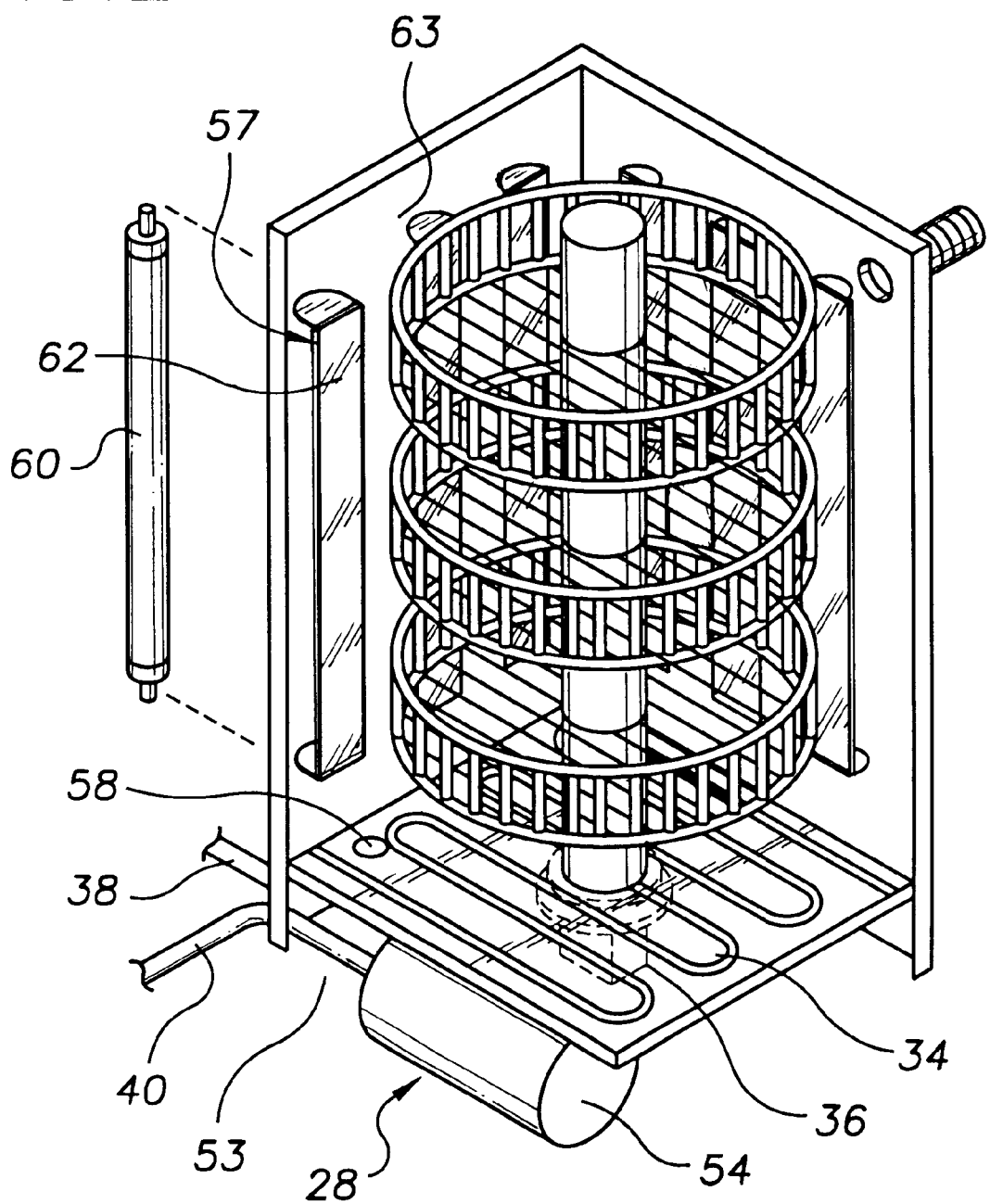
FIG. 2 is a cut-away perspective view of the interior of the toy washer and disinfector device showing the bottom surface and two of the defining walls of the washing and disinfecting chamber showing the chamber heating element, the spray tower pump unit positioned beneath the washing and disinfecting chamber and in connection with the spray tower; the bleaching unit reservoir and return opening; the water supply and sewer drain lines, and the exhaust vent.

FIG. 1 shows an exemplary embodiment of the toy washer and disinfector device of the present invention, generally designated by the numeral 10. Toy washer and disinfector device 10 includes a housing, generally designated 12, including a lower housing portion 14 and an upper housing portion 16; a washing and disinfecting chamber, generally designated 18, formed within lower housing portion 14; a sealable chamber access door 20; a light disinfection mechanism, generally designated 22; three user removable, rotatable item racks 24 rotatably disposed on a conventional spray tower 26; a washing soap dispensing assembly 30; a dryer mechanism, generally designated 32; a timer and function controller, generally designated 42; and referring to FIG. 2, a chemical disinfecting mechanism, generally designated 28; a resistance heating element 34; a spray tower pump unit, generally designated 36, a water supply control valve 38, and a sewer drain line control valve 40.

Dryer mechanism 32 includes a heated air dryer blower 50 (FIG. 1) and a separately activated exhaust opening 52 (FIG. 1). Chemical disinfecting mechanism 28 includes a bleach pump 53, a bleach reservoir 54, a bleach dispensing orifice 56 (FIG. 1) and a return opening 58. Light disinfecting mechanism 22 includes a number of ultra-violet light disinfecting assemblies, generally designated 57, that each include a fluorescent ultraviolet light 60 and a tempered glass window 61 set into the interior chamber walls 63 that define washing and disinfecting chamber 18.

Figure 3:
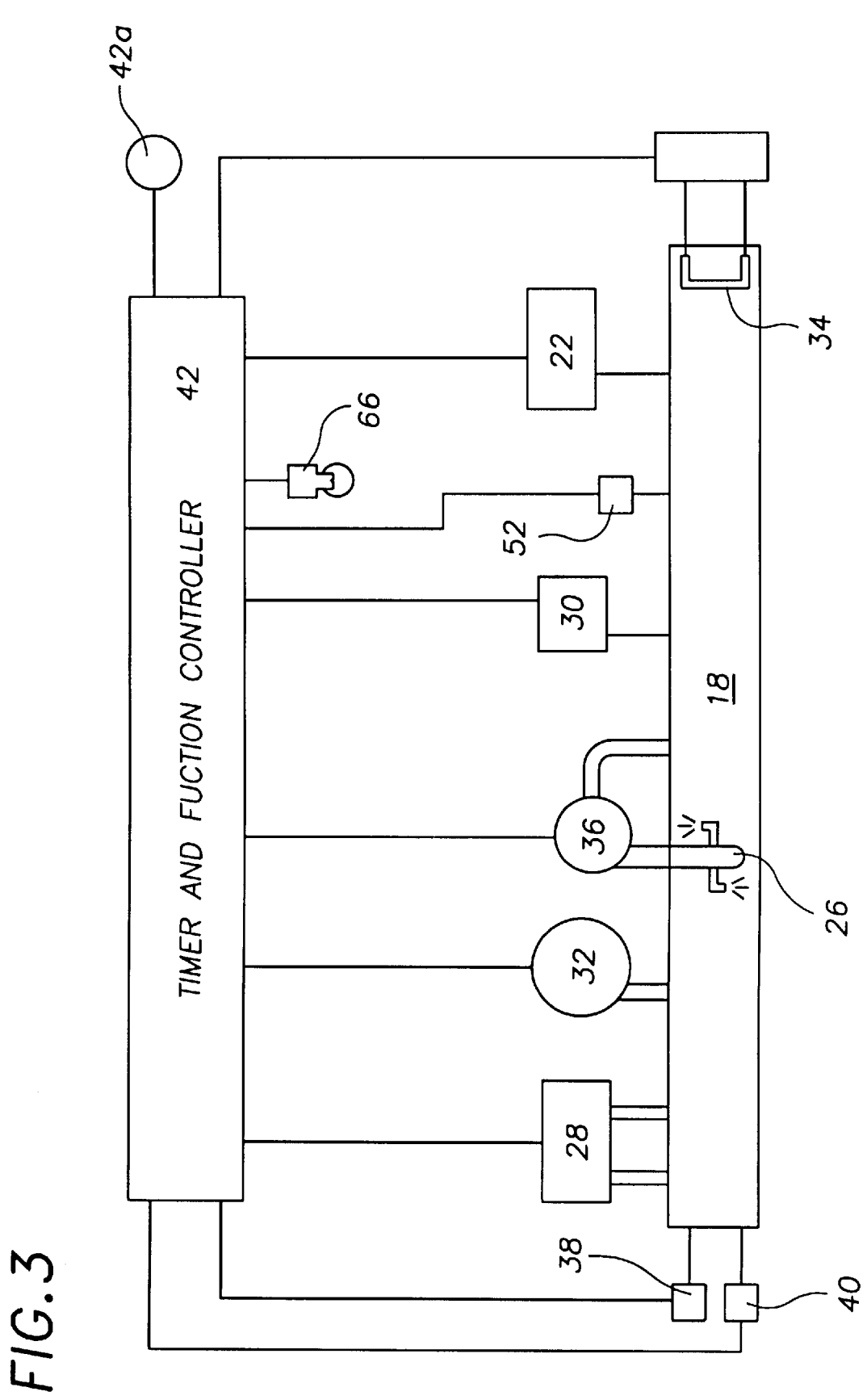
FIG. 3 is a schematic diagram of the toy washer and disinfector device of FIG. 1 showing the washing and disinfecting chamber; the water supply control valve; the sewer line drain control valve; the bleaching unit mechanism including the bleach storage reservoir, the bleach pump, the bleach dispensing opening, and the bleach return opening; the dryer mechanism including the forced heated air blower; the dryer exhaust vent; the spray tower in connection with the spray tower pump unit; the washing soap dispensing assembly; the ultraviolet light disinfecting mechanism; the chamber heating element; the defective ultraviolet light indicator lamp; the on/off switch.

With reference now to FIG. 3, timer and function controller 42 is a conventional microprocessor based appliance timer and function controller having an on/off switch 42a and that is in controlling connection with light disinfection mechanism 22, chemical disinfecting mechanism 28, washing soap dispensing assembly 30, dryer mechanism 32, resistance heating element 34, spray tower pump unit 36, water supply control valve 38, and sewer drain line control valve 40; and that is programmed to control a light disinfection cycle, a chemical disinfecting cycle, a soap wash cycle, a clean water rinse cycle, and a drying cycle.

The soap wash cycle includes dispensing soap from washing soap dispensing assembly 30, introducing water into washing and disinfecting chamber 18 through water supply control valve 38, heating the water to a desired temperature if necessary with resistance heating element 34, operating spray tower pump unit 36 to spray pressurized, heated water and washing soap streams onto toys positioned on rotatable item racks 24 or otherwise within washing and disinfecting chamber 18 for a predetermined washing period, and then draining washing and disinfecting chamber 18 sewer drain line control valve 40.

The clean water rinse cycle includes introducing clean water into washing and disinfecting chamber 18 through water supply control valve 38, heating the water to a desired temperature if necessary with resistance heating element 34, operating spray tower pump unit 36 to spray pressurized, heated water streams onto toys positioned on rotatable item racks 24 or otherwise within washing and disinfecting chamber 18 for a predetermined rinsing period, and then draining washing and disinfecting chamber 18 through sewer drain line control valve 40.

The drying cycle includes operating the dryer blower 50 FIG. 1 while the exhaust opening 52 is in the opening position for a predetermined drying period. If desired, resistance heating element 34 is operated to provide additional heat with washing and disinfecting chamber 18 during the drying cycle.

The chemical disinfecting cycle includes operating the bleach pump to pump a quantity of bleach from bleach reservoir 54 into washing and disinfecting chamber 18 through bleach dispensing orifice 56; operating spray tower pump unit 36 to spray pressurized, bleach streams onto toys positioned on rotatable item racks 24 or otherwise within washing and disinfecting chamber 18 for a predetermined chemical disinfecting period; and then draining washing and disinfecting chamber 18 of excess bleach and returning the excess bleach to bleaching unit reservoir 54 through return opening 58.

The light disinfecting cycle includes operating fluorescent ultraviolet lights 60 of light disinfection mechanism 22, so that ultra-violet wavelength light shines on the toys positioned within washing and disinfecting chamber 18 for a period of time to have a disinfectant effect. In this embodiment, defective ultraviolet light indicator lamp 66 becomes illuminated when one or more of the fluorescent ultraviolet lights 60 fails to illuminate.

It can be seen from the preceding description that a toy washer and disinfector device has been provided that can clean multiple toys; that operates automatically; that has removable toy racks that are positionable within a washing and disinfecting chamber; and that includes a housing assembly including a lower housing portion and an upper housing portion; a washing and disinfecting chamber formed within the lower housing portion; a water supply control valve for supplying water to the washing and disinfecting chamber; a sewer line drain control valve for draining water and soap from the washing and disinfecting chamber; a sealable chamber access door pivotally connected to the lower housing portion; a light disinfection mechanism including a plurality of ultraviolet light disinfecting assemblies, each ultraviolet light disinfecting assembly including a tempered glass window set into the interior chamber wall and an ultraviolet emitting light; a plurality of user removable, rotatable item racks rotatably disposed on a spray tower positioned within the washing and disinfecting chamber; a spray tower pump unit including an inlet in connection with the washing and disinfecting chamber and an outlet in connection with the spray tower; a chemical disinfecting mechanism including a bleaching unit having a bleach reservoir, a bleach dispensing pump, and a bleach dispensing nozzle; a washing soap dispensing assembly; a dryer mechanism including a forced heated air blower and exhaust vent; a chamber heating element positioned within the washing and disinfecting chamber; and timer and function controls positioned within the upper housing portion, including a defective ultraviolet light indicator lamp and an on/off switch, and in controlling connection with the light disinfection mechanism, the chemical disinfecting mechanism, the washing soap dispensing assembly, the dryer mechanism, the heating element, the spray tower pump unit, the water supply valve, and the sewer drain line valve; the timer and function controls controlling a light disinfection cycle, a chemical disinfecting cycle, a soap wash and clean water rinse cycle, and a drying cycle.

It is noted that the embodiment of the toy washer and disinfector device described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A toy washer and disinfector device comprising:

said toy washer and disinfector device including a housing assembly including a lower housing portion and an upper housing portion;

a washing and disinfecting chamber formed within said lower housing portion;

a water supply control valve for supplying water to said washing and disinfecting chamber;

a sewer line drain control valve for draining water and soap from said washing and disinfecting chamber;

a sealable chamber access door pivotally connected to said lower housing portion;

a light disinfection mechanism including a plurality of ultraviolet light disinfecting assemblies, each ultraviolet light disinfecting assembly including a tempered glass window set into said interior chamber wall and an ultraviolet emitting light;

a plurality of user removable, rotatable item racks rotatably disposed on a spray tower positioned within said washing and disinfecting chamber;

a spray tower pump unit including an inlet in connection with said washing and disinfecting chamber and an outlet in connection with said spray tower;

a chemical disinfecting mechanism including a bleaching unit having a bleach reservoir, a bleach dispensing pump, a bleach dispensing nozzle and a return opening in connection between said bleach reservoir and said washing and disinfecting chamber for returning excess bleach pumped from said bleach reservoir by said bleach dispensing pump into said washing and disinfecting chamber at an end of a chemical disinfecting cycle after a period of operating said spray tower pump unit to spray bleach over items within said washing and disinfecting chamber;

a washing soap dispensing assembly;

a dryer mechanism including a forced heated air blower and exhaust vent;

a chamber heating element positioned within said washing and disinfecting chamber;

and timer and function controls positioned within said upper housing portion, including a defective ultraviolet light indicator lamp and an on/off switch, and in controlling connection with said light disinfection mechanism, said chemical disinfecting mechanism, said washing soap dispensing assembly, said dryer mechanism, said heating element, said spray tower pump unit, said water supply valve, and said sewer drain line valve;

said timer and function controls controlling a light disinfection cycle, said chemical disinfecting cycle, a soap wash cycle, a clean water rinse cycle, and a drying cycle.

* * * * *